(12) United States Patent
Campbell

(10) Patent No.: US 7,452,343 B2
(45) Date of Patent: Nov. 18, 2008

(54) ANKLE SUPPORT

(75) Inventor: Frank W. Campbell, Oakdale, MN (US)

(73) Assignee: Swede-O, Inc., North Branch, MN (US)

( * ) Notice: Subject to any disclaimer, the term of this patent is extended or adjusted under 35 U.S.C. 154(b) by 1122 days.

(21) Appl. No.: 10/636,793

(22) Filed: Aug. 7, 2003

(65) Prior Publication Data

US 2005/0033216 A1 Feb. 10, 2005

(51) Int. Cl.
*A61F 5/00* (2006.01)
(52) U.S. Cl. .......................................... 602/23; 602/27
(58) Field of Classification Search .................. 602/5, 602/23, 27; 128/877–879, 882; 482/121, 482/129
See application file for complete search history.

(56) References Cited

U.S. PATENT DOCUMENTS

| | | | |
|---|---|---|---|
| 4,527,556 A | 7/1985 | Nelson | |
| 5,025,802 A * | 6/1991 | Laico et al. | 128/882 |
| 5,472,000 A * | 12/1995 | Olsen | 128/878 |
| 5,782,727 A * | 7/1998 | Pierce | 482/129 |
| 5,971,946 A | 10/1999 | Quinn et al. | |
| 6,368,258 B1 * | 4/2002 | Emlaw | 482/124 |
| 6,398,750 B1 | 6/2002 | Quinn et al. | |
| 6,663,583 B1 | 12/2003 | Janis | |

* cited by examiner

*Primary Examiner*—Michael Brown
(74) *Attorney, Agent, or Firm*—IPLM Group, P.A.

(57) ABSTRACT

An ankle support utilizes a strap having a first end and a second end. The first end forms a loop adapted to go around a user's foot and the second end is adapted to go around the user, proximate the user's ankle. A loop member is operatively connected to the first end and the second end passes through the loop member, whereby pulling on the second end tightens both the first end and the second end. In other embodiments, the ankle support may utilize a body being operatively connected thereto. In other embodiments, the ankle support is operatively connected to a shoe.

29 Claims, 11 Drawing Sheets

ANKLE SUPPORT

BACKGROUND OF THE INVENTION

1. Field of the Invention

This invention relates generally to an ankle brace and more particularly an ankle support having a strap member with two opposing ends that are slidably connected and pulling on one end tightens up both ends.

2. Description of the Prior Art

The human ankle consists of three bones, the tibia, the fibula, and the talus, which are bound to the bones of the foot and to one another by ligaments. The particular arrangement of the three bones allows the foot to rotate about three orthogonal axes relative to the leg. The ligaments place elastic limits on the extent of such rotation or movement.

Many ankle injuries occur when ankle movement exceeds the elastic limit of one or more ligaments. One relatively common ankle injury, known as eversion of the ankle, results when the ankle moves too far outward as the foot rolls over. Another relatively common ankle injury, known as inversion of the ankle, results when the ankle moves too far inward as the foot rolls over. Many individuals, and athletes in particular, require external support for their ankles as a result of previous eversion or inversion injuries or ongoing concerns about adequately protecting their ankles.

A common practice among athletes is to tightly wrap the ankles with medical adhesive tape. Although "taping" is generally recognized as an effective way to protect a weak or injured ankle, it suffers several drawbacks, as well. For example, an effective tape job necessarily restricts movement of the foot in all directions relative to the leg, thereby limiting desirable ankle motions as well as undesirable ones. Taping is also relatively costly because the tape is typically used only once, and it often requires a trainer to be properly applied.

Fabric ankle wraps are sometimes used as an alternative to taping. The fabric wraps may be used more than once, but their elasticity and lack of adhesiveness renders them less effective than medical tape in terms of immobilizing the joint.

A variety of relatively rigid support structures have been designed as alternatives to medical tape and fabric wraps. However, those skilled in the art continue to seek improvements in areas such as reliable support, user comfort, user mobility, application simplicity, and/or manufacturing cost.

SUMMARY OF THE INVENTION

In one embodiment, the invention is an ankle support for use in supporting an ankle bone and ankle joint. The support includes a body adapted and configured to embrace a user's ankle. A strap has a first end, second end and an intermediate section. The intermediate section is secured to the body. An attachment member is operatively connected to the body, the first end slidably secured to the attachment member, wherein the strap forms a loop adapted to go around the user's foot. The second end is adapted to go around the user, proximate the user's ankle. A loop member is operatively connected to the first end, and the second end passes through the loop member, wherein pulling on the second end tightens both the first end and the second end. A first securing mechanism is provided for keeping the second end in a tightened position.

In another embodiment, the invention is an ankle support for use in supporting an ankle bone and ankle joint. The support includes a body adapted and configured to be wrapped around a user's ankle and secured in position. A strap has a first end, second end and intermediate section. The intermediate section is secured to the body. The first end forms a first loop adapted to be positioned around the user's foot and a second end forming a second loop positioned around the user's ankle, thereby forming a FIG. 8 configuration. A connecting member is provided for connecting the first end to the second end, wherein pulling on the second end tightens both the first and second ends around the user's ankle and foot.

In another embodiment, the invention is an ankle support for use in supporting an ankle bone and ankle joint. The support includes a body adapted and configured to embrace a user's ankle. The body has an elongate member having an inner side and an outer side and an adjustable fastener operatively connected to the elongate member, whereby the elongate member is adjustable in size to fit a variety of users having different sized feet and ankle joints. A strap has a first end, second end and intermediate section. The intermediate section is secured to the outer side of the body. The first end forms a first loop adapted to be positioned around the user's foot and a second end forming a second loop positioned around the user's ankle thereby forming a FIG. 8 configuration. A loop member is operatively connected to the first end and the second passes through the loop member, wherein pulling on the second end tightens both the first and second ends. A securing mechanism is provided for keeping the second end in a tightened position.

In another embodiment, the invention is an ankle support for use in supporting an ankle bone and ankle joint. The support includes a body adapted and configured to embrace a user's ankle. A strap has a first segment, the first segment operatively connected to the body member and having an unsecured first end. The strap has a second segment, the second segment operatively connected to the body member and having an unsecured second end. An attachment member is secured to the body, the first end slidably secured to the attachment member, wherein the strap forms a first loop adapted to go around the user's foot. The second end is adapted to go around the user, proximate the user's ankle. A loop member is operatively connected to the first end and the second end passes through the loop member, wherein pulling on the second end tightens both the first end and the second end. A first securing mechanism for keeping the second end in a tightened position is provided.

In another embodiment, the invention is an ankle support for use in supporting an ankle bone and ankle joint. The support includes a body adapted and configured to embrace a user's ankle. An attachment member is operatively connected to the strap. The first end is slidably secured to the attachment member, wherein the strap forms a first loop adapted to go around a user's foot. A second end is adapted to go around the user, proximate the user's ankle. A loop member is operatively connected to the first end and the second end passing through the loop member, wherein pulling on the second end tightens both the first end and second end. A first securing mechanism is provided for keeping the second end in a tightened position.

In another embodiment, the invention is a shoe and ankle support combination. The combination includes a sole and an upper section operatively connected to the sole. The upper section having an opening to allow a user to insert the user's foot into the shoe. An ankle support is operatively connected to the shoe. The ankle support includes a strap having a first end, intermediate section and a second end. The intermediate section encircles the opening and crosses in front of the upper section. The first end is positioned around the user's foot. A loop member is operatively connected to the first end and the second end passing through the loop member, wherein pulling on the second end tightens both the first end and second end. A securing mechanism is provided for keeping the first end in a tightened position.

DETAILED DESCRIPTION OF THE PREFERRED EMBODIMENT

Figure 1:
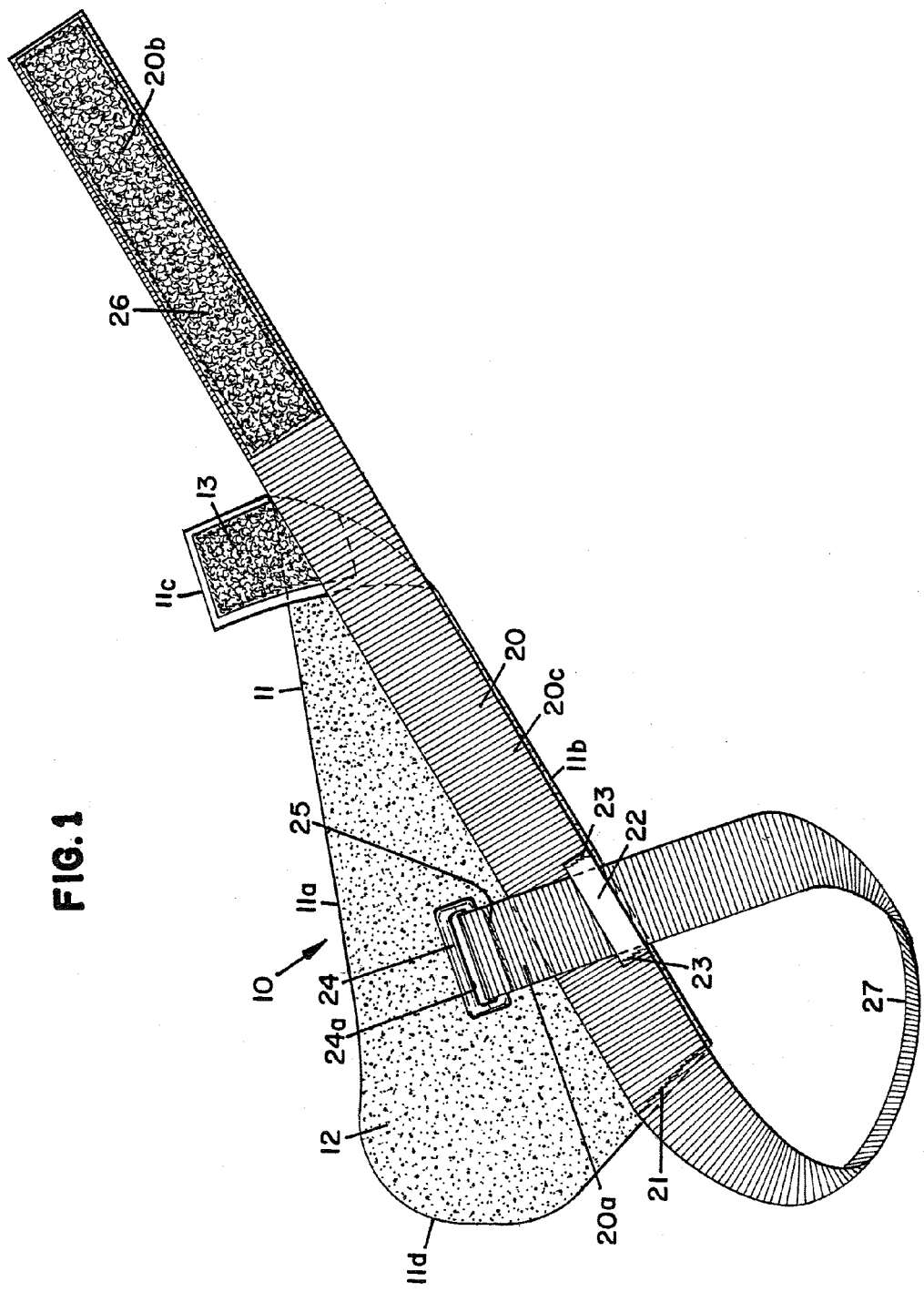
FIG. 1 is a top plan view of the ankle support constructed according to the principals of the present invention.

Referring to the drawing, wherein like numerals represent like parts throughout the several views, there is generally disclosed at 10 an ankle support. The ankle support 10 includes a body member 11. The body 11 is constructed from a suitable material such as neoprene. The body 11 is able to stretch slightly so as to provide for a tighter wrap around the user's ankle, but it is not necessary that it does stretch. The body member 11 is able to be stretched from 1-2 inches under normal tension by a user. The body member 11 is covered on its outer surface by a loop material 12. A rectangular piece of hook material 13 is operatively connected to the other side of the body member 11. The loop material 12 and hook material 13 may be any suitable material such as Velcro® material. The body 11 has a generally upper edge 11a and a bottom edge 11b. The width of the body member 11 decreases, as viewed in FIG. 1, as it extends to the end 11c. The end 11d is wider than the opposite end 11c. As will be discussed more fully hereafter, the shape of the body member 11 is adapted and configured to be wrapped around and secured about the foot of a user.

A strap 20 has a first end 20a and a second end 20b. Between the ends 20a, 20b is an intermediate section 20c. The strap 20 is shown as a single continuous strap. However, as will be discussed more fully hereafter, there are other embodiments that may be utilized. The intermediate section 20c is secured to the body member by suitable means such as stitching. As shown in FIG. 1, stitching 21 secures the strap to the body member 11 at one location. An attachment member 22 is secured to both the strap 20 and a body member 11 by stitching 23, at two locations. The stitching 23 goes through the attachment member 22, strap 20 and body 11. This forms an opening through which the first end 20a is slidable. A generally rectangular loop member 24 is secured to the first end 20a by suitable means such as stitching 25. The loop member 24 has an opening 24a through which the second end 20b is slidable. A hook material 26 is secured to one side of the strap 20 proximate the second end 20b. The strap 20 is generally made from a non-stretching material such as a polyester webbing material. However, it is recognized that some stretch may be acceptable. The attachment member 22 is shown as an additional member. It is understood that other embodiments may also be used for the attachment member 22.

Figure 6:
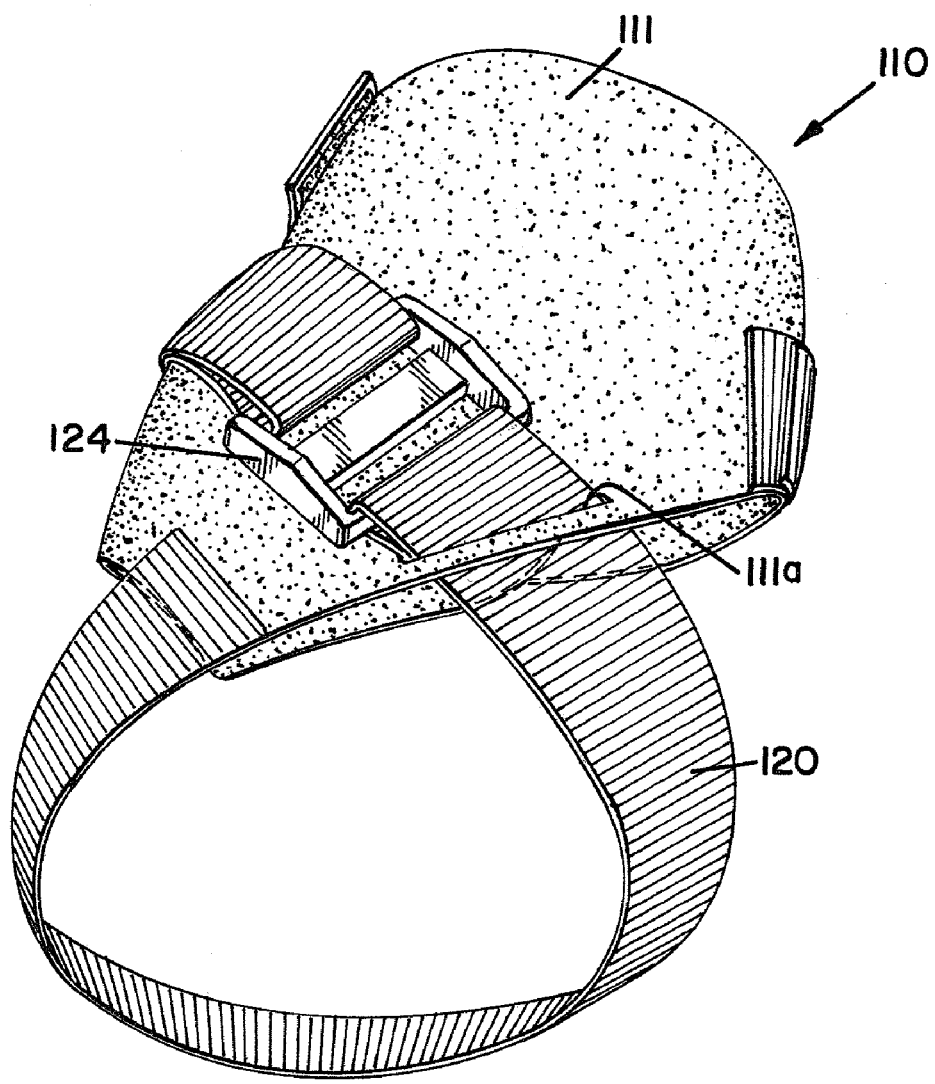
FIG. 6 is a perspective view of another embodiment of the present invention.

Another embodiment of the present invention is shown in FIG. 6 and shows an ankle support 110. This embodiment shows another method of using an attachment member, which serves as the same function as attachment member 22 in the first embodiment. The ankle support 110 is identical to the ankle support 10 and therefore only the differences will be discussed hereafter. The loop member 124 is of a different design but performs the same function as the loop member 24. This is only a change of the type of loop member being shown. The one change of significance is that the body member 111 has a slot 111a formed therein. The slot 111a is approximately the same position as the attachment member 22 was in the first embodiment, but is not used in this embodiment. Here the strap 120 is threaded through the slot 111a. The slot 111a therefore functions as the attachment member 22 and is another example of an attachment member.

Figure 7:
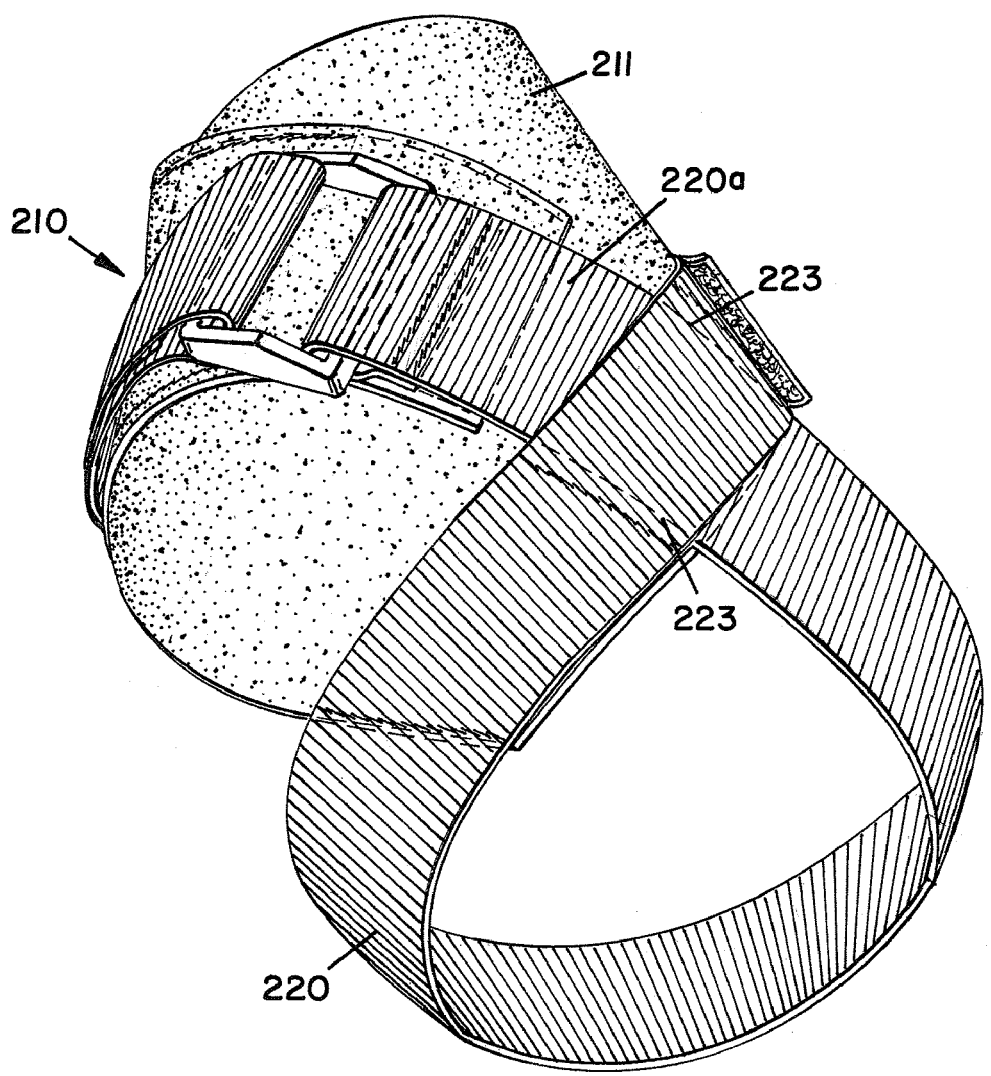
FIG. 7 is a perspective view of another embodiment of the present invention.

Still another embodiment of this invention is shown in FIG. 7 where an ankle support 210 is shown. In this embodiment of the ankle support 210, the attachment member 22 of the first embodiment is not a separate member. Again, since the ankle support 210 is substantially the same as the ankle support 10, only the differences will be discussed hereafter. In the embodiment shown for ankle support 210, there is no attachment member 22. Instead, the stitching 223 is extended the width of the strap 220 and forms a sleeve between the body 211 and strap 223 in which the first end 220a may be inserted. This sleeve would then hold the first end 220a in position, similar to the strap member 22. It is understood the stitching 223 does not have to extend the entire width.

Figure 2:
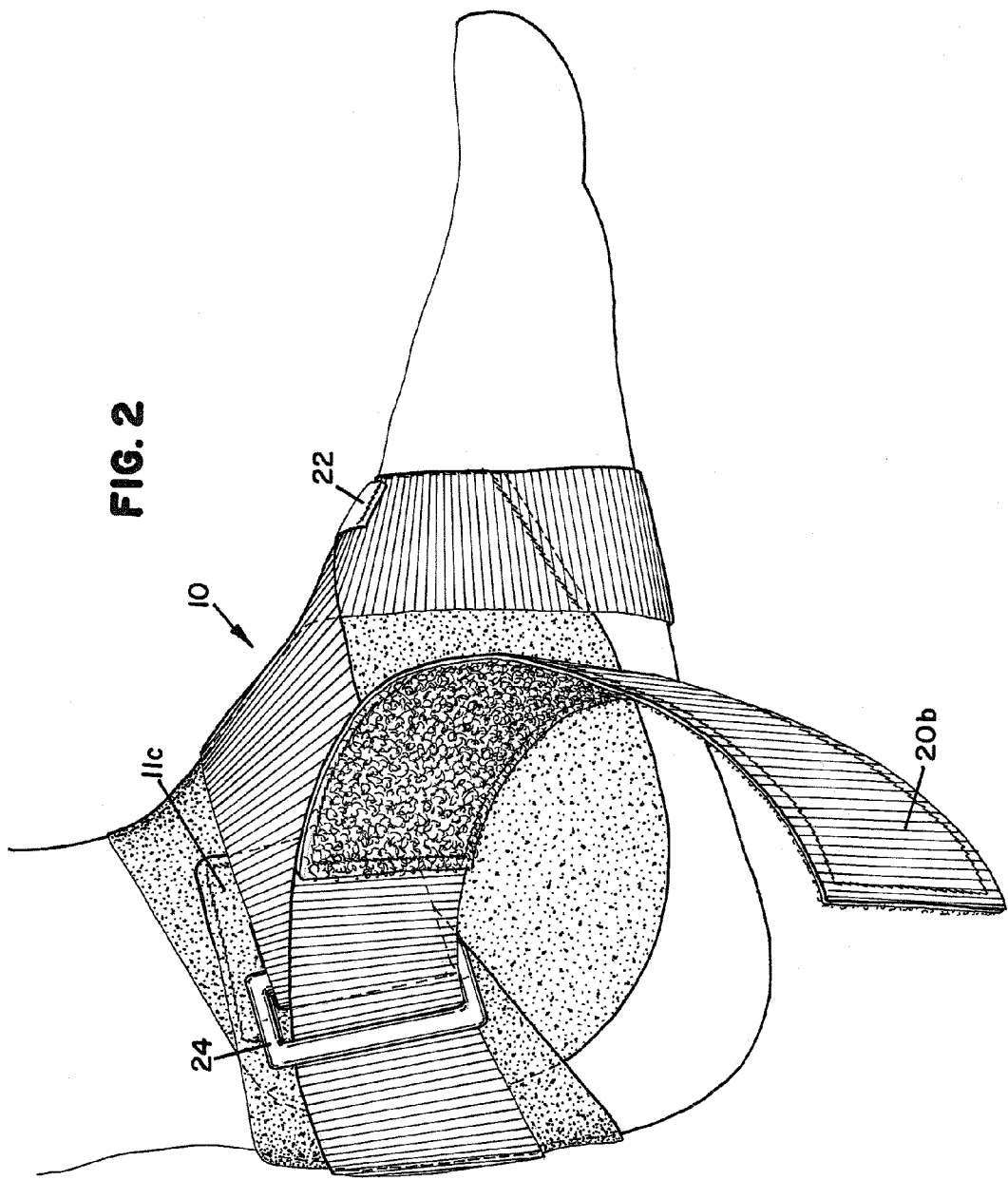
FIG. 2 is a side elevational view of the ankle support, shown in FIG. 1, on a wearer's foot, not tensioned.
Figure 3:
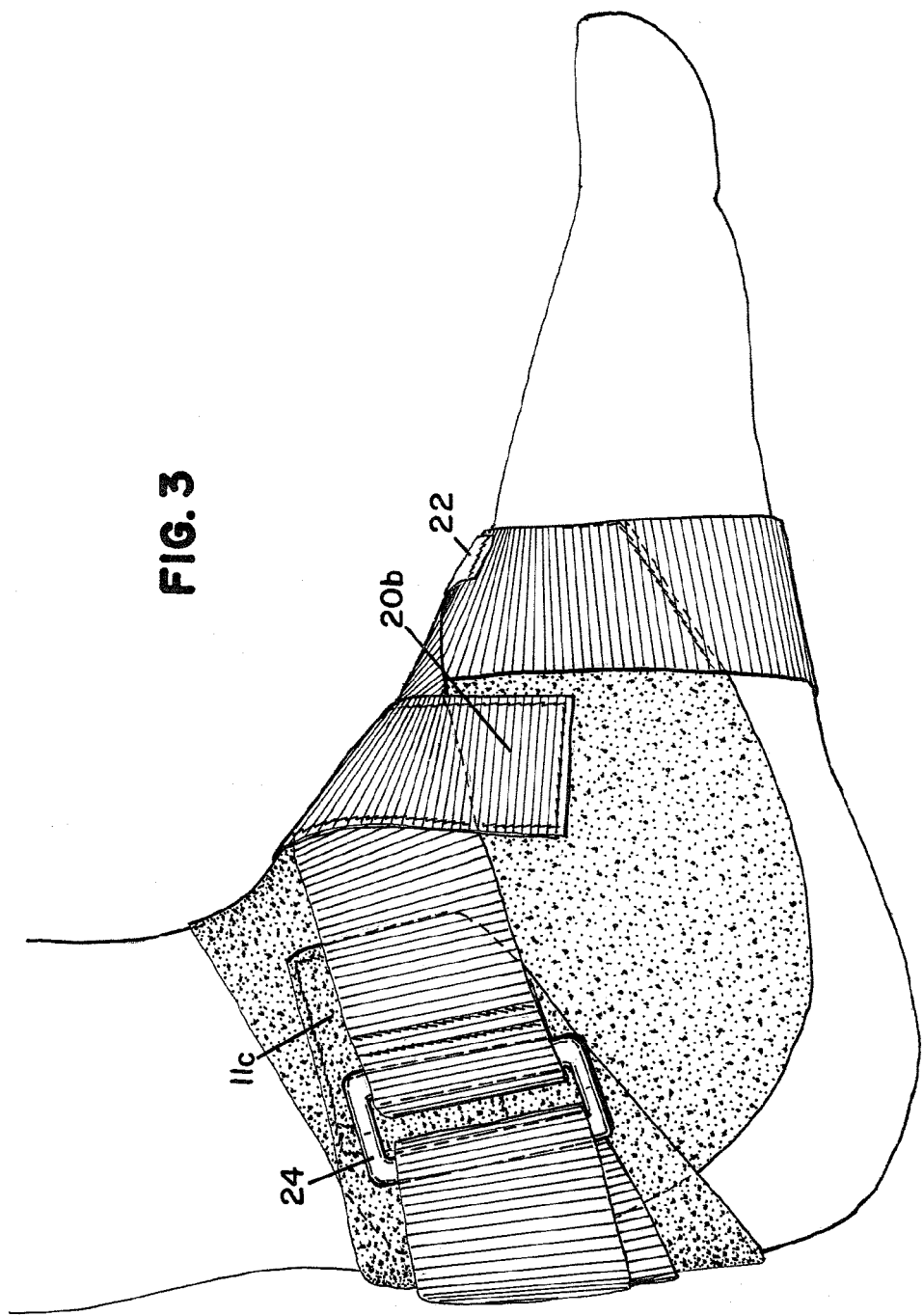
FIG. 3 is a side elevational view of the ankle support, shown in FIG. 1, on a wearer's foot, tensioned.

FIG. 2 shows the ankle support 10 around the foot of a user before tensioning. In preparing to place the ankle support 10 on the foot, the loop member 24 is passed between the opening between the attachment member 22 and the strap 20, as shown in FIG. 1. This provides for the opening 27 through which the toes of the user are inserted. The loop 27 then encircles the foot, approximately in the position shown in FIG. 2. At that point, the end 11c is wrapped around behind the foot and secured to the hook material 12 on the body member 11 thereby encircling the ankle, forming a generally cylindrical support around the user's leg and ankle. The second end 20b is then looped around the back of the user's leg and inserted into the loop 24. Referring now to FIG. 3, the end 20b is brought backwards, approximately 180 degrees from the direction that it was inserted into the loop 24. The user then pulls back on the strap end 20b thereby tightening not only the second end 20b, but also pulling on the first end 20a, thereby tightening both ends 20a, 20b. The second end 20b is then wrapped around back around the ankle and secured to the loop material 12 on the body member 11, as shown in FIG. 3. It is understood that other suitable fasteners, such as snaps, may be utilized to secure body member 11 on itself, as well as the strap 20 to the body member.

The present invention allows for a simple and effective ankle support that may be used on either the right or left foot. Further, the support is able to be utilized on different size feet. The overall length of the body member 11 is sufficient to cover a wide range of feet size. The distance between the ends 11c and 11d is sufficient to cover a variety of sizes. Any extra length can just be wrapped further around the user's leg. Similarly, the strap 20 is sufficient to accommodate a variety of foot sizes. One example of a suitable strap length would be approximately 33 inches, while it is understood that other suitable lengths may also be used. Further, the length of the body member would be approximately 12 inches in length and 6 inches in height, at its highest point. Again, other suitable dimensions may be utilized.

Figure 5:
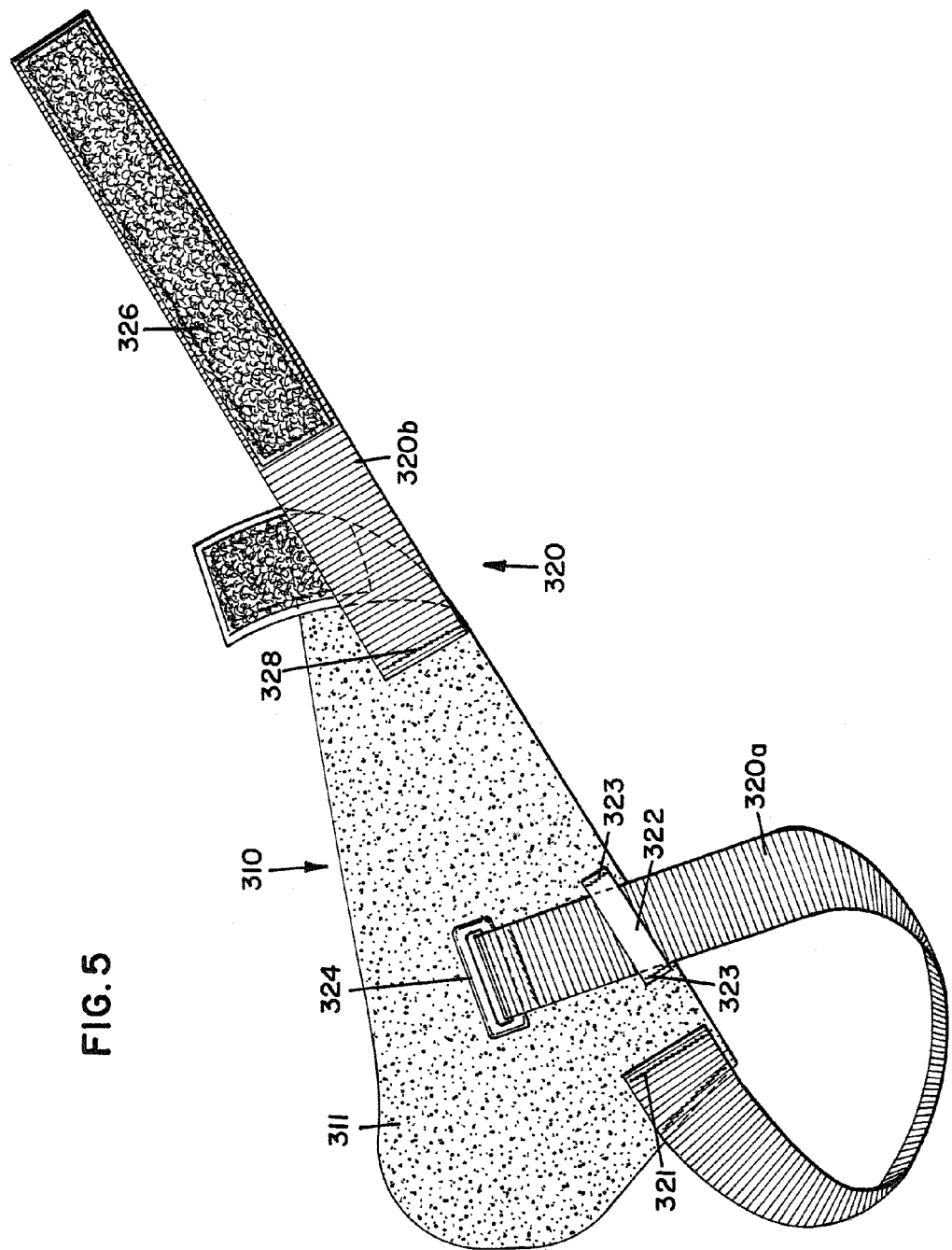
FIG. 5 is a top plan view of another embodiment of the ankle support of the present invention.

The strap 20 has been described as a single strap. However, it is recognized that the strap does not have to be continuous. That is, the first end of the strap 20*a* may be discontinued after the stitching 21. Further, that portion of the strap, as viewed in FIG. 1, to the left of stitching 23, is not necessary. What is required is that there be only two free ends that interact so that the pulling on one end tightens both ends, as previously described. An embodiment incorporating a non-continuous strap is shown in FIG. 5, which shows the ankle support 310. The ankle support 310 includes a strap, generally designated at 320, which includes a first section 320*a* and a second section 320*b*. An attachment member 322 is secured to the body member 311 by stitching 323, at two locations. This forms an opening through which one end of the first section 320*a* is slidable. The opening formed by the stitching 323 is sized so that the loop member 324 has to be forced through the opening. Then, the opening prevents the loop member 324 from being removed during normal use. The other end of the first section 320*a* is secured to the body 311 by stitching 321 at two locations. The second section 320*b* is secured at one end to the body 311 by stitching 328. A hook material 326 is secured to one side of the second section 320*b*. The strap 320 is generally made from a non-stretch material such as a polyester webbing material. However, it is recognized that some stretch may be acceptable. As can be seen, this ankle support 310 is very similar to the first embodiment of the ankle support 10 with the exception that the strap 320 is not continuous.

Figure 4:
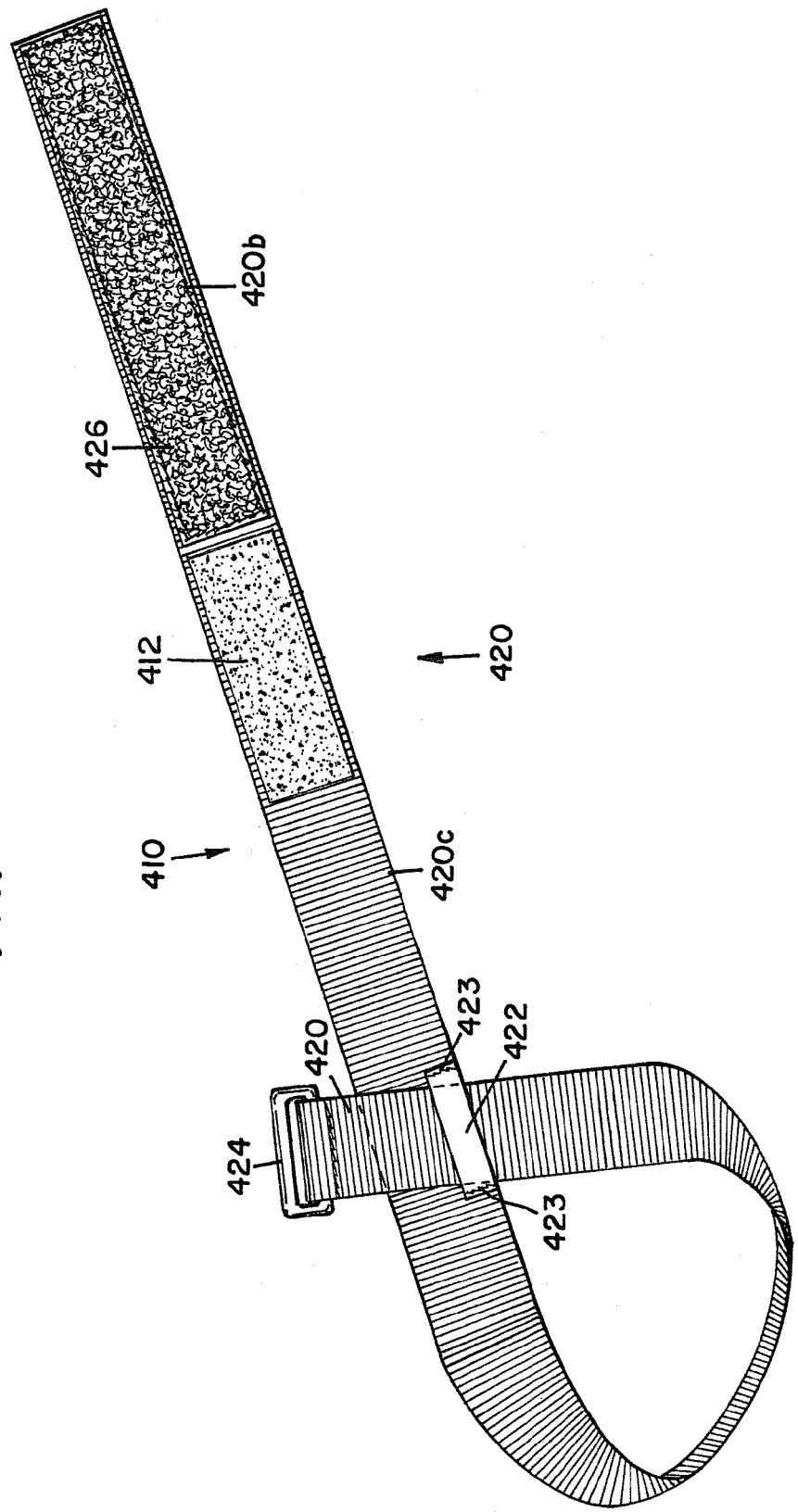
FIG. 4 is a top plan view of another embodiment of the present invention.

Another embodiment of an ankle support 410 is shown in FIG. 4. The ankle support 410 is the same as the ankle support 10 shown in FIG. 1 without the body member 11. The ankle support 410 includes only the strap 420 which is similar to strap 20. The ankle support 420 is utilized the same as the embodiment shown in FIGS. 1-3 except that there is no body portion. The ankle support 410 is used as the same as described previously for ankle support 10. A strap 420 has a first end 420*a*, intermediate section 420*c* and a second end 420*b* on which is secured hook material 426. An attachment member 422 is held in position by stitching 423 and a loop member 424 is operatively connected to the first end 420*a*. The only difference between the strap 420 and the strap 20 is the addition of loop material 412 that is added adjacent the hoop material 426 and that the attachment member 422 is secured to the strap and not a body. Therefore, when the second end 420*b* is tightened up around the loop member 424, the hook material 426 is fastened to the loop material 412, thereby securing the strap 420 in position. It is also understood that other types of fastening mechanisms may be utilized for this and other embodiments described. One such fastening member would be a self-locking loop member, as will be discussed more fully with respect to the additional embodiments to be described hereinafter.

Figure 8:
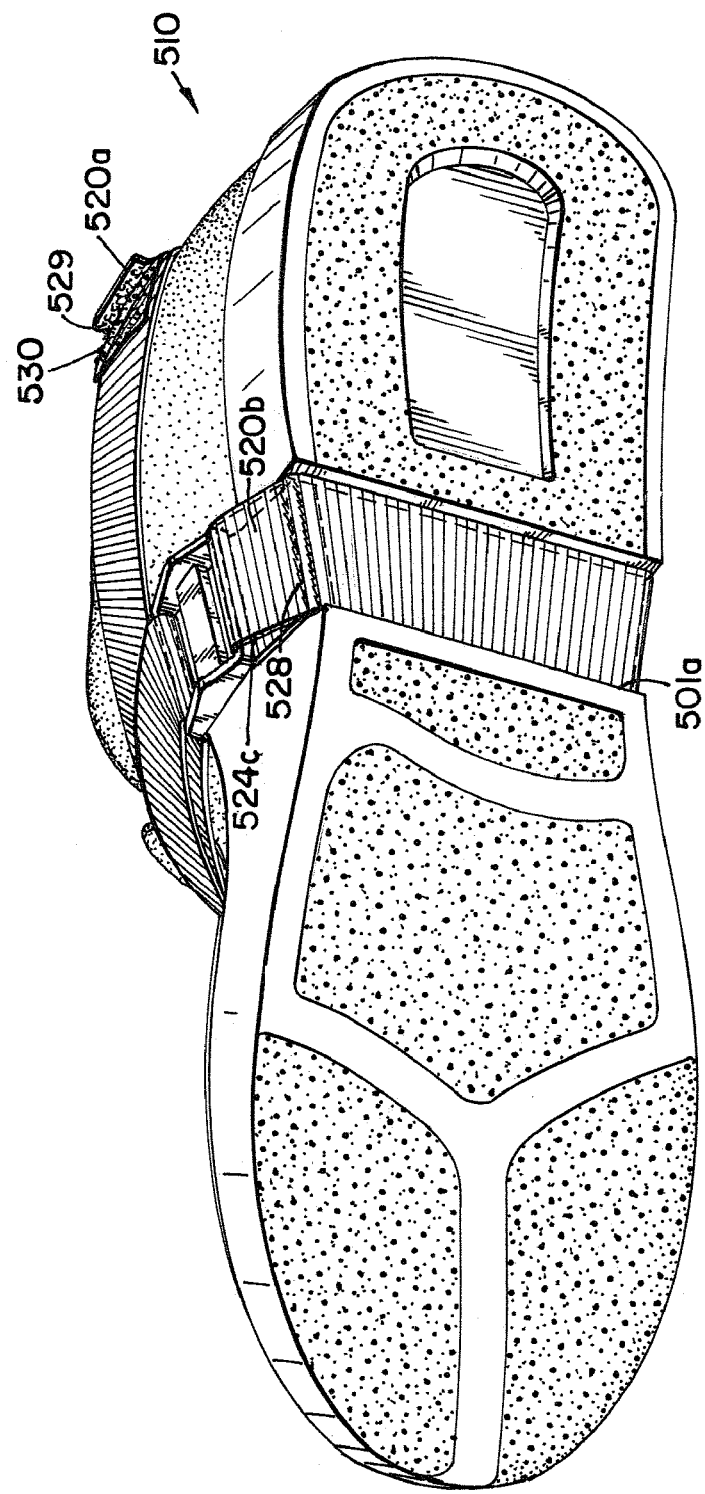
FIG. 8 is a bottom perspective view of another embodiment of the present invention.
Figure 9:
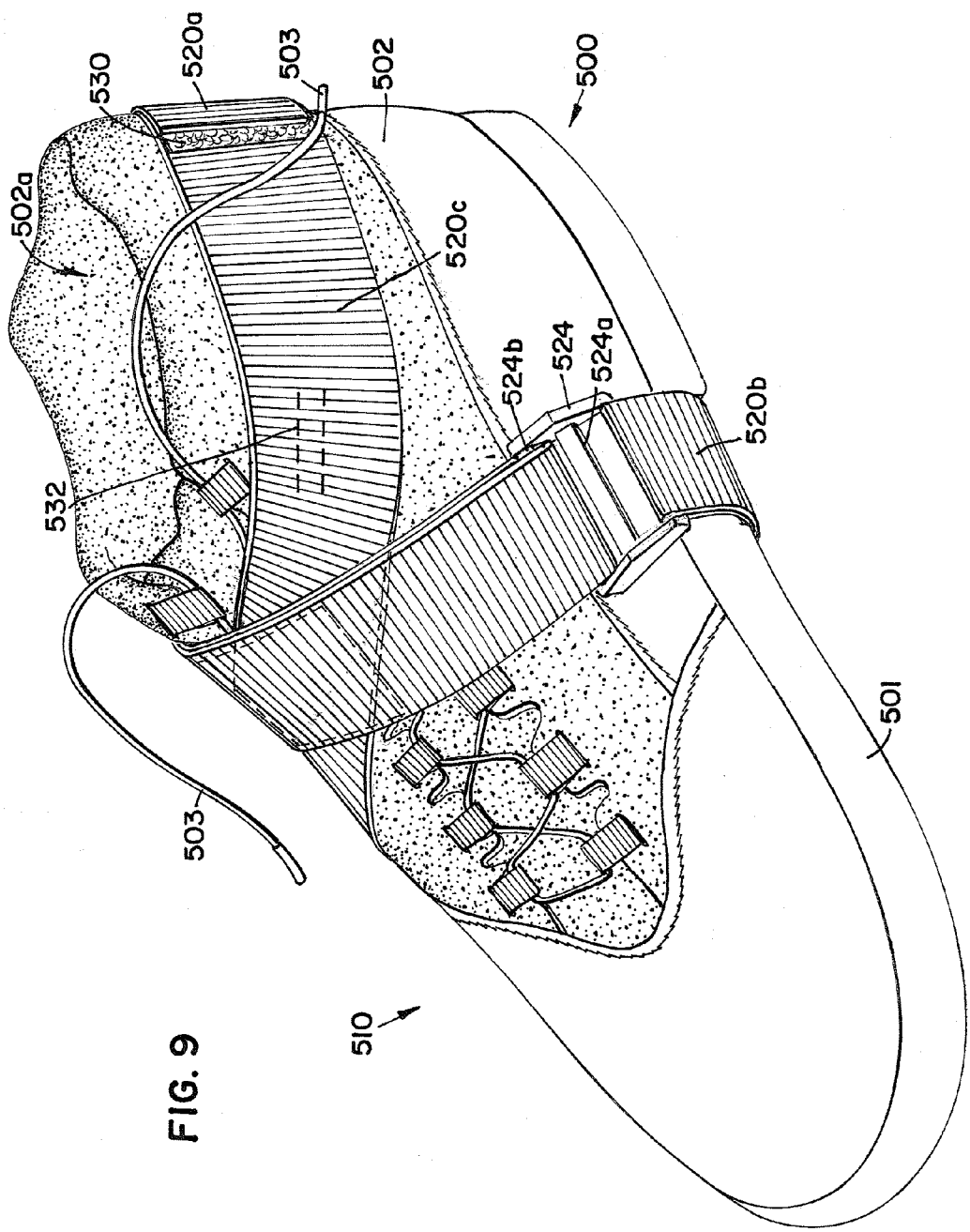
FIG. 9 is a top perspective of the embodiment shown in FIG. 8.

In addition, there are other embodiments of the present invention. These embodiments include the incorporation of the strap into a shoe, such as a tennis shoe or other athletic shoe. In this embodiment, the body member 11 is replaced by the shoe. One embodiment incorporating the strap into a shoe is shown in FIGS. 8 and 9. Another embodiment incorporating the strap into a shoe is shown in FIGS. 10 and 11.

Referring now to FIGS. 8 and 9, a shoe an ankle support combination 510 is shown. The shoe 500 includes a sole 501 operatively connected to an upper section 502 by means well known in the art. The upper section 502 includes an opening 502*a* through which a user places his foot. Shoe laces 503 are used to secure the shoe 500 to the user's foot. Such a construction is well known in the art and the details thereof are not included, but are well known. A strap 520 is operatively connected to the shoe 500.

The strap 520 includes a first end 520*a*, a second end 520*b* and an intermediate section 520*c* between the two ends. The strap 520 is operatively connected to a loop member 524. The loop member 524 is generally rectangular having a top bar 524*b*, bottom bar 524*c* and a cross bar 524*a*. The second end 520*b* is looped around the bottom bar 524*c* of the loop member 524 and secured by stitching 528 to itself. The strap 520 continues from the loop member 524 and goes underneath the sole 501. The sole 501 has an indentation 501*a* so that the thickness of the strap 520 does not protrude beyond the base of the sole 501. Therefore, the strap 520 does not interfere with the traction of the shoe 500. The strap then goes underneath the sole, and comes back across the front of the shoe 500 on top of the front portion of the upper section 502. The intermediate portion of the strap 520*c* then continues around the back of the shoe 500 (the heel) and then around the shoe 500 and then crosses over the intermediate section 520*c* back down to the loop member 524. The strap 520 goes underneath the top bar 524*b* of the loop member 524 and is pulled back across the front of the shoe to tighten both ends of the strap 520. The hook material 529, operatively connected to the underneath side of the first end 520*a*, is secured to loop member 530 on the intermediate section 520*a* to hold the strap in position. Again, the strap 520 operates similar to the previously described straps. That is, after the strap has been looped underneath the loop member 524 and is pulled across, the pulling on the one end 520*a* tightens both ends that are connected to the loop member 524, thereby tightening both ends at the same time. The intermediate section 520*c* is operatively connected to the upper section 502 by stitching 532. It is understood that the strap 520 could be secured in more than one position and in any other suitable way.

Figure 10:
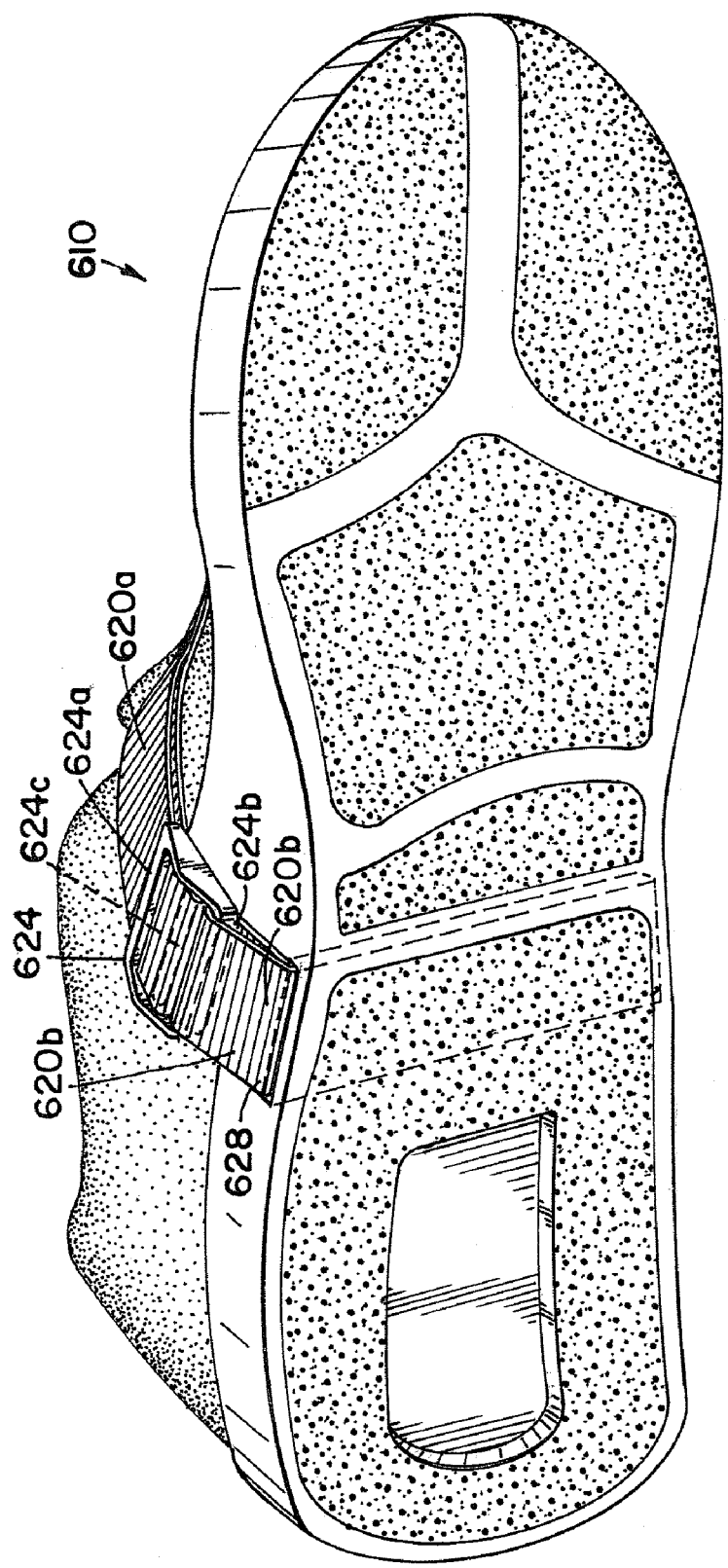
FIG. 10 is a perspective view of another embodiment of the present invention.
Figure 11:
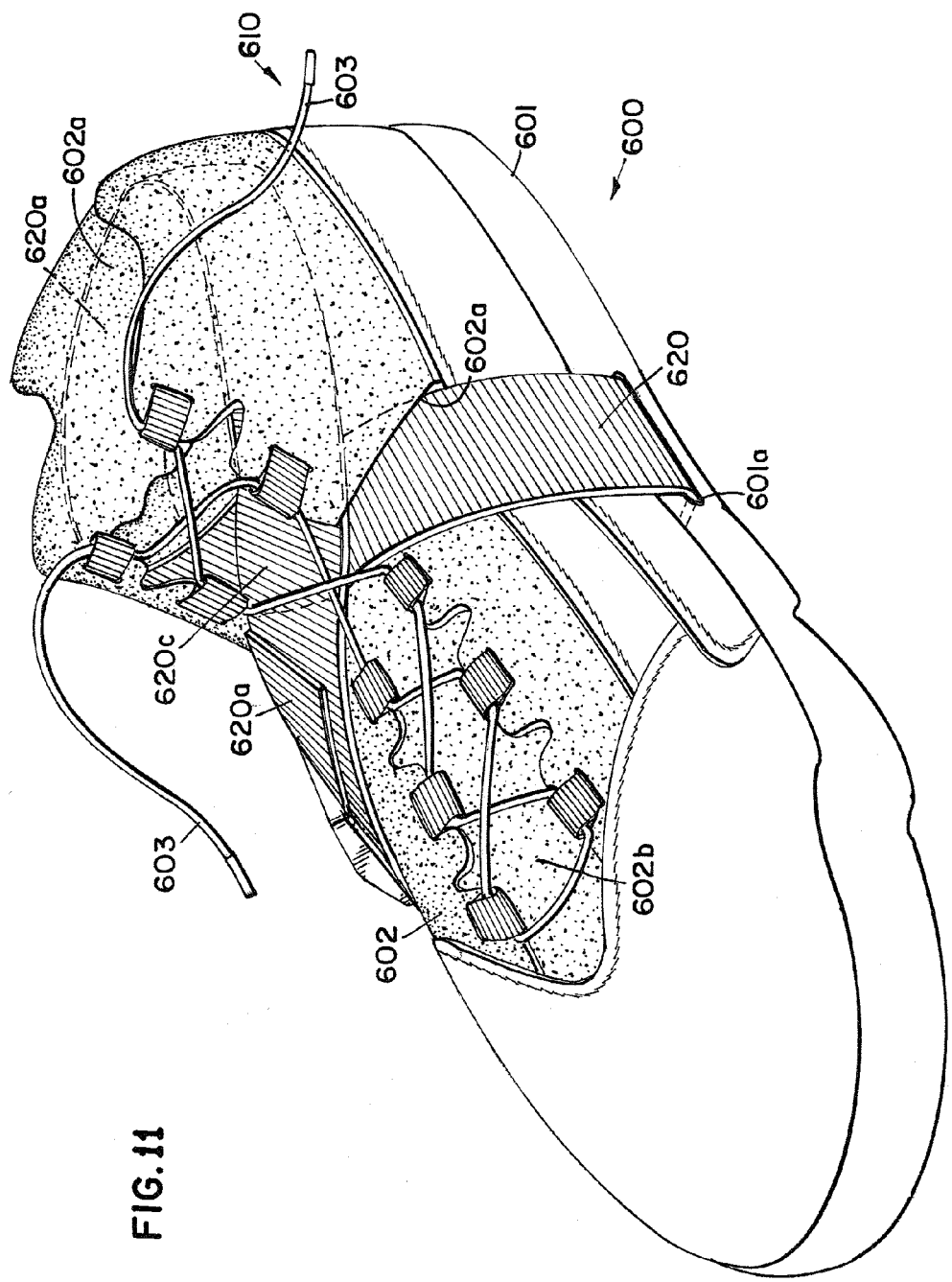
FIG. 11 is a top perspective of the embodiment shown in FIG. 10.

Another embodiment showing an ankle support and shoe combination is generally designated as 610 and is shown in FIGS. 10 and 11. The combination 610 includes a shoe, generally designated as 600 and a strap 620.

The shoe 600 may be any suitable shoe, such as a tennis shoe or other athletic shoe, and includes a sole 601 operatively connected to an upper section 602. The upper section 602 has an opening 602*a* through which a user's foot may be placed. Shoe laces 603 are used to secure the shoe around the user's foot. The shoe and ankle support combination 610 is similar to the shoe and ankle support combination 510, with the exception that the strap 620 has more portions of the strap internal to the shoe 600. Also, a different manner of securing the strap 620 to the loop member 624 is utilized as will be discussed more fully hereafter. Further, the loop member 624 is considered a self-locking loop member in the industry and may also be utilized with the other embodiments previously described.

A strap 620 includes a first end 620*a*, a second end 620*b* and an intermediate section 620*c*, which is between the two ends 620*a* and 620*b*. The loop member 624 is the same as loop member 524. However, because of the way the strap 620 is threaded through the loop member 624, the loop member 624 is self-locking. The loop member 624 is generally rectangular in shape and has a top bar 624*a* and a bottom bar 624*b*. A middle cross bar 624*c* is shown in dashed lines, as it is hidden by the strap 620. However, the cross bar 624*c* is the same as cross bar 524*a*, shown in FIG. 9. The second end 620*b* is secured to the bottom bar 624*b* by the second end 620*b* being looped around the bottom bar 624b and stitched by stitching 628 to form a loop. The strap 620 then continues underneath the shoe 600 by being threaded through an elongate slot formed in the sole 601. The strap then comes out of the slot 601a on the other side of the shoe and continues up the inside of the shoe 600 and crosses in the front of the shoe. A slot 602a is formed in the upper section to allow the strap 620 to lay flat as it crosses underneath the shoe laces 603 and on top of the tongue 602b. The strap then encircles the heel area of the upper section 602. The intermediate section 620c, at this point, is preferably inside of the upper section 602 (between an inner surface and outer surface of the upper section 602), so as not to contact the user's ankle. The strap 620 then comes out of the ankle area and crosses on top of the other portion of the strap 620 and goes to the loop member 624. The first end 620a goes underneath the loop member 26 and around the cross bar 624c. The first end 620a then goes up and over the cross bar 624c and back underneath the top bar 624a. Then, as with the other embodiments, the first end 620a can be pulled in one direction and tighten both the first end 620a and second end 620b at the same time. Since the locking member 624 is self-locking, there is not the need to utilize the hook and loop fastener to fasten the first end 620a in a tightened position. The foregoing are just two examples of how the strap of the present invention may be utilized in combination with a shoe, it being understood that other suitable methods may be used to operatively connect a strap, incorporating the present invention, into a shoe and provide for a shoe and ankle support combination.

The above specification, examples and data provide a complete description of the manufacture and use of the composition of the invention. Since many embodiments of the invention can be made without departing from the spirit and scope of the invention, the invention resides in the claims hereinafter appended.

I claim:

1. An ankle support for use in supporting an ankle bone and ankle joint, comprising:
    a) a body adapted and configured to embrace a user's ankle;
    b) a strap having a first end, second end and an intermediate section;
    c) the intermediate section secured to the body;
    d) an attachment member operatively connected to the body, said first end slidably secured to the attachment member, wherein the strap forms a first loop adapted to go around the user's foot;
    e) the second end adapted to go around the user, proximate the user's ankle;
    f) a loop member operatively connected to the first end and the second end passing through the loop member, wherein pulling on the second end tightens both the first end and the second end; and
    g) a first securing mechanism for keeping the second end in a tightened position.

2. The ankle support of claim 1, wherein the attachment member is a slot formed in the body.

3. The ankle support of claim 1, wherein the attachment member comprises first and second fastening members, the fastening members connecting the intermediate section to the body at spaced intervals, thereby forming an opening through which the first end is slidably secured.

4. The ankle support of claim 1, wherein the strap is a continuous member.

5. The ankle support of claim 1, the body comprising:
    a) an elongate member having an inner side and an outer side; and
    b) an adjustable fastener operatively connected to the elongate member, whereby the elongate member is adjustable in size to fit a variety of users having different sized feet and ankle joints.

6. The ankle support of claim 5, the adjustable fastener comprising a hook material on one of said sides and a loop material on the other of said sides.

7. The ankle support of claim 5, the intermediate section is secured to the outer side of the body.

8. The ankle support of claim 5, the first loop, from the intermediate section to the first end, is in a first clockwise direction and the second loop, from the intermediate section to the second end, is in a second clockwise direction which is opposite the first clockwise direction.

9. The ankle brace of claim 1, the securing mechanism comprising:
    a) the second end having a first side and a second side; and
    b) a hook material on one of said sides and a loop material on the other of said sides, wherein the strap is adjustable in size to fit a variety of users having different sized feet.

10. An ankle support for use in supporting an ankle bone and ankle joint, comprising:
    a) a body adapted and configured to be wrapped around a user's ankle and secured in position;
    b) a strap having a first end, second end and an intermediate section;
    c) the intermediate section secured to the body;
    d) the first end forming a first loop adapted to be positioned around the user's foot and the second end forming a second loop positioned around the user's ankle, thereby forming a FIG. 8 configuration; and
    e) a connecting member for connecting the first end to the second end, wherein pulling on the second end tightens both the first end and second end around the user's ankle and foot.

11. The ankle support of claim 10, wherein the strap is a continuous member.

12. The ankle support of claim 10, the body comprising:
    a) an elongate member having an inner side and an outer side; and
    b) an adjustable fastener operatively connected to the elongate member, whereby the elongate member is adjustable in size to fit a variety of users having different sized feet.

13. The ankle support of claim 12, the adjustable fastener comprising a hook material on one of said sides and a loop material on the other of said sides.

14. The ankle support of claim 12, the intermediate section is secured to the outer side of the body.

15. The ankle support of claim 12, the first loop, from the intermediate section to the first end, is in a first clockwise direction.

16. The ankle support of claim 15, the second loop, from the intermediate section to the second end, is in a second clockwise direction which is opposite the first clockwise direction.

17. The ankle support of claim 10, the connecting member comprising:
    a) a loop member operatively connected to the first end and the second end passing through the loop member;
    b) the second end having a first side and a second side; and
    c) a hook material on one of said sides and a loop material on the other of said sides, wherein the strap is adjustable in size to fit a variety of users having different sized feet.

18. An ankle support for use in supporting an ankle bone and ankle joint, comprising:
   a) a body adapted and configured to embrace a user's ankle, the body having an elongate member having an inner side and an outer side and an adjustable fastener operatively connected to the elongate member, whereby the elongate member is adjustable in size to fit a variety of users having different sized feet and ankle joints;
   b) a strap having a first end, second end and an intermediate section, the intermediate section is secured to the outer side of the body;
   c) the first end forming a first loop adapted to be positioned around the user's foot and the second end forming a second loop positioned around the user's ankle, thereby forming a FIG. 8 configuration;
   d) a loop member operatively connected to the first end and the second end passing through the loop member, wherein pulling on the second end tightens both the first end and the second end; and
   e) a first securing mechanism for the keeping the second end in a tightened position.

19. The ankle support of claim 18, the adjustable fastener comprising a hook material on one of said sides and a loop material on the other of said sides.

20. The ankle support of claim 19, the securing mechanism comprising:
   a) the second end having a first side and a second side; and
   b) a hook material on one of said sides and a loop material on the other of said sides, wherein the strap is adjustable in size to fit a variety of users having different sized feet.

21. An ankle support for use in supporting an ankle bone and ankle joint, comprising:
   a) a body adapted and configured to embrace a user's ankle;
   b) a strap having a first segment, the first segment operatively connected to the body member and having an unsecured first end;
   c) the strap having a second segment, the second segment operatively connected to the body member and having an unsecured second end;
   d) an attachment member secured to the body, said first end slidably secured to the attachment member, wherein the strap forms a first loop adapted to go around the user's foot;
   e) the second end adapted to go around the user, proximate the user's ankle;
   f) a loop member operatively connected to the first end and the second end passing through the loop member, wherein pulling on the second end tightens both the first end and the second end; and
   g) a first securing mechanism for the keeping the second end in a tightened position.

22. The ankle support of claim 21, wherein the strap is a continuous member.

23. The ankle support of claim 21, the body comprising:
   a) an elongate member having an inner side and an outer side; and
   b) an adjustable fastener operatively connected to the elongate member, whereby the elongate member is adjustable in size to fit a variety of users having different sized feet and ankle joints.

24. An ankle support for use in supporting an ankle bone and ankle joint, comprising:
   a) a body adapted and configured to embrace a user's ankle;
   b) an attachment member operatively connected to the strap, the first end slidably secured to the attachment member, wherein the strap forms a first loop adapted to go around a user's foot;
   c) the second end adapted to go around the user, proximate the user's ankle;
   d) a loop member operatively connected to the first end and the second end passing through the loop member, wherein pulling on the second end tightens both the first end and the second end; and
   e) a first securing mechanism for keeping the second end in a tightened position.

25. The ankle support of claim 24, wherein the attachment member is a slot formed in the body.

26. The ankle support of claim 24, the first loop, from the intermediate section to the first end, is in a first clockwise direction and the second loop, from the intermediate section to the second end is in a second clockwise direction which is opposite the first clockwise direction.

27. An ankle support for use in supporting an ankle bone and ankle joint, comprising:
   a) a strap having a first end, second end and an intermediate section;
   b) an attachment member operatively connected to the intermediate section, said first end slidably secured to the attachment member, wherein the strap forms a first loop adapted to go around the user's foot;
   c) the second end adapted to go around the user, proximate the user's ankle;
   d) a loop member operatively connected to the first end and the second end passing through the loop member, wherein pulling on the second end tightens both the first end and the second end; and
   e) a first securing mechanism for keeping the second end in a tightened position.

28. The ankle support of claim 27, wherein the attachment member is a slot formed in the intermediate member.

29. The ankle support of claim 27, wherein the attachment member comprises first and second fastening members, the fastening members connecting the intermediate section to the body at spaced intervals, thereby forming an opening through which the first end is slidably secured.

* * * * *